(12) United States Patent
Tass et al.

(10) Patent No.: US 9,302,069 B2
(45) Date of Patent: Apr. 5, 2016

(54) DEVICE AND METHOD FOR VISUAL STIMULATION

(75) Inventors: Peter A. Tass, Munich (DE); Birgit Utako Barnikol, Titz (DE); Christian Hauptmann, Stolberg (DE); Karim Haroud, Chavannes-sur-Moudon/Vd (CH); Jean-Christophe Roulet, Ligniéres/NE (CH); Urban Schnell, Muenchenbuchsee/Be (CH)

(73) Assignees: Forschungszentrum Juelich GmbH, Juelich (DE); Universitaet zu Koeln, Cologne (DE)

( * ) Notice: Subject to any disclaimer, the term of this patent is extended or adjusted under 35 U.S.C. 154(b) by 1129 days.

(21) Appl. No.: 12/875,619

(22) Filed: Sep. 3, 2010

(65) Prior Publication Data
US 2010/0331912 A1     Dec. 30, 2010

Related U.S. Application Data

(63) Continuation of application No. PCT/DE2009/000303, filed on Mar. 4, 2009.

(30) Foreign Application Priority Data

Mar. 5, 2008   (DE) .......................... 10 2008 012 669

(51) Int. Cl.
*A61N 1/18*   (2006.01)
*A61M 21/00*  (2006.01)
(Continued)

(52) U.S. Cl.
CPC ............. *A61M 21/00* (2013.01); *A61N 5/0618* (2013.01); *A61M 2021/0044* (2013.01);
(Continued)

(58) Field of Classification Search
CPC .................................................. A61N 1/36082
USPC .................................. 128/898; 607/54, 88, 89
See application file for complete search history.

(56) References Cited

U.S. PATENT DOCUMENTS 4,926,969 A * 5/1990 Wright et al. ................. 600/544
5,219,322 A    6/1993 Weathers
(Continued)

FOREIGN PATENT DOCUMENTS

DE       195 43 405 A1   5/1997
DE       19905145 A1     8/2000
(Continued)

OTHER PUBLICATIONS

Brian A. Wendell et al.; "Visual Field Maps in Human Cortex"; Neuron Review, 56, Oct. 25, 2007, pp. 366-383.
(Continued)

Primary Examiner — William Thomson
Assistant Examiner — Jeffrey Lipitz
(74) Attorney, Agent, or Firm — Arent Fox LLP

(57) ABSTRACT

A device and method for providing stimulation signals that reset the phase of the neuronal activity of neurons in a patient's brain. The device includes a control unit; and a stimulation unit that has a plurality of stimulation elements, and each stimulation element generates visual stimulation signals that reset the phase of the neuronal activity of the neurons when the signals are taken up via an eye of a patient and transmitted to neurons that are exhibiting a pathologically synchronous and oscillatory neuronal activity. The control unit is further capable of actuating the stimulation unit such that the stimulation elements generate the visual stimulation signals with a time offset in respect to one another and/or with differing phase and/or with differing polarity.

16 Claims, 12 Drawing Sheets

(51) Int. Cl.
*A61N 5/06* (2006.01)
*A61N 5/073* (2006.01)

(52) U.S. Cl.
CPC . *A61M 2205/332* (2013.01); *A61M 2205/3569* (2013.01); *A61M 2230/10* (2013.01); *A61M 2230/16* (2013.01); *A61M 2230/30* (2013.01); *A61M 2230/40* (2013.01); *A61M 2230/60* (2013.01); *A61M 2230/65* (2013.01); *A61N 5/0622* (2013.01); *A61N 2005/0648* (2013.01); *A61N 2005/073* (2013.01)

(56) References Cited

U.S. PATENT DOCUMENTS

| | | | |
|---|---|---|---|
| 5,409,445 | A | 4/1995 | Rubins |
| 5,599,274 | A | 2/1997 | Widjaja et al. |
| 5,709,645 | A * | 1/1998 | Siever .......................... 600/27 |
| 2003/0181961 | A1 | 9/2003 | Kamei |
| 2005/0088617 | A1 * | 4/2005 | Hsieh et al. .................. 351/205 |
| 2006/0106276 | A1 | 5/2006 | Shealy et al. |

FOREIGN PATENT DOCUMENTS

| | | |
|---|---|---|
| DE | 10110004 B4 | 6/2006 |
| DE | 10233960 B4 | 11/2006 |
| GB | 2 393 786 A | 4/2004 |
| WO | WO-0164005 A3 | 6/2002 |

OTHER PUBLICATIONS

European Search Report dated Oct. 4, 2012. (English Translation).
M.E. Brandt; "Visual and auditory evoked phase resetting of the alpha EEG"; International Journal of Psychophysiology 26 (1997), pp. 285-298.
F.H.L da Silva; "Event-related neural activites: what about phase?"; Progress in Brain Research, vol. 159, 2006, pp. 3-17.
A. Mazaheri and O. Jensen; "Posterior α activity is not phase-reset by visual stimuli"; PNAS, vol. 103, Feb. 21, 2006, pp. 2948-2952.

* cited by examiner

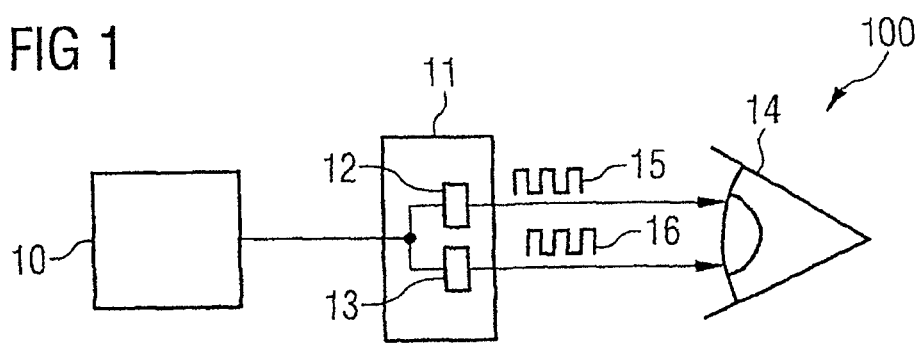
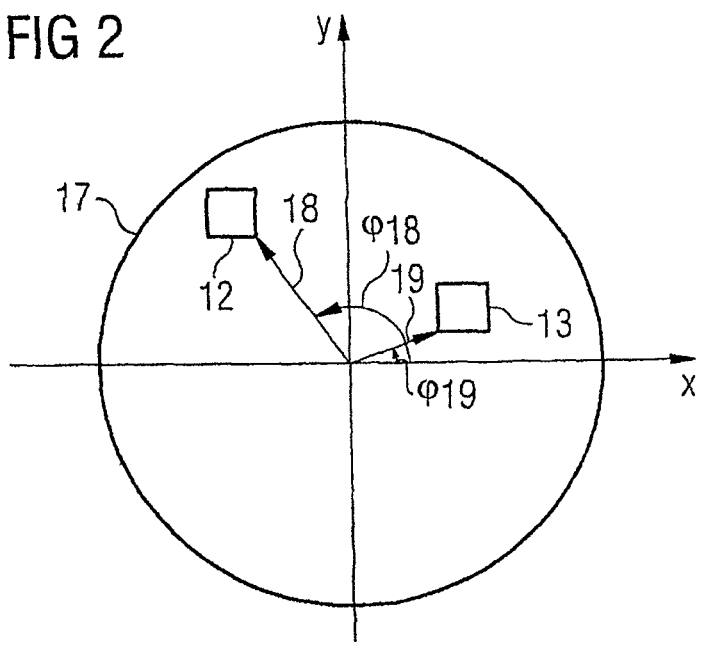
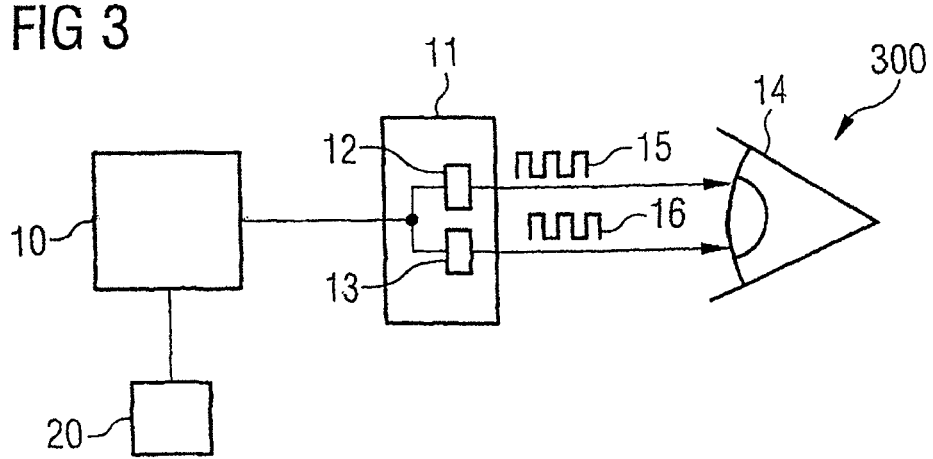

DEVICE AND METHOD FOR VISUAL STIMULATION

BACKGROUND

There are excessively strong neuronal activity synchronization procedures in the brain in a number of neurological and psychiatric diseases and these have a very strong negative influence on the cerebral function. Currently available therapy methods for such diseases include e.g. pharmacotherapy and deep brain stimulation.

SUMMARY

The present application is directed to a device and method for providing stimulation signals that reset the phase of the neuronal activity of neurons in a patient's brain. The device includes a control unit; and a stimulation unit that has a plurality of stimulation elements, and each stimulation element generates visual stimulation signals that reset the phase of the neuronal activity of the neurons when the signals are taken up via an eye of a patient and transmitted to neurons that are exhibiting a pathologically synchronous and oscillatory neuronal activity. The control unit is further capable of actuating the stimulation unit such that the stimulation elements generate the visual stimulation signals with a time offset in respect to one another and/or with differing phase and/or with differing polarity.

In another aspect of the present application, a device is provided having a control unit; and a stimulation unit including a plurality of stimulation elements configured to generate visual stimulation signals, wherein the stimulation signals are taken up via an eye of a patient and are transmitted to different sites in a neuron population having a pathologically synchronous and oscillatory neuronal activity, and wherein the stimulation signals bring about a resetting at different times of the phase of the neuronal activity of the neurons at the different sites in the neuron population.

In further aspect of the present application a method is providing including the steps of generating visual stimulation signals; and taking up the stimulation signals via an eye of a patient and are transmitted to different sites in a neuron population having a pathologically synchronous and oscillatory neuronal activity, wherein the stimulation signals bring about a resetting at different times of the phase of the neuronal activity of the neurons at the different sites in the neuron population.

In yet a further aspect of the application, a device is provided having a control unit; and a stimulation unit including a plurality of stimulation elements provided to generate visual stimulation signals that influence the phase of the neuronal activity of the neurons when said signals are received via an eye of a patient and transmitted to neurons, which exhibit a pathologically synchronous and oscillatory neuronal activity, wherein the control unit is configured to actuate the stimulation unit such that at least two of the stimulation elements generate the visual stimulation signals with different frequencies.

In yet another aspect of the application, a device is provided having a measurement unit configured to measure measurement signals on a patient; a stimulation unit configured to generate visual stimulation signals; and a control unit configured to actuate the stimulation unit on the basis of the measurement signals such that the stimulation unit converts the measurement signals into visual stimulation signals.

In another aspect of the application, a method is provided including the steps of measuring measurement signals on a patient; and generating visual stimulation signals by a stimulation unit, wherein the stimulation unit is actuated on the basis of the measurement signals such that the stimulation unit converts the measurement signals into the visual stimulation signals.

BRIEF DESCRIPTION OF THE DRAWINGS

FIG. 1 shows a schematic illustration of a device 100 as per an exemplary embodiment.

FIG. 2 shows a schematic illustration of the visual field of a patient.

FIG. 3 shows a schematic illustration of a device 300 as per a further exemplary embodiment.

DETAILED DESCRIPTION

Figure 4:
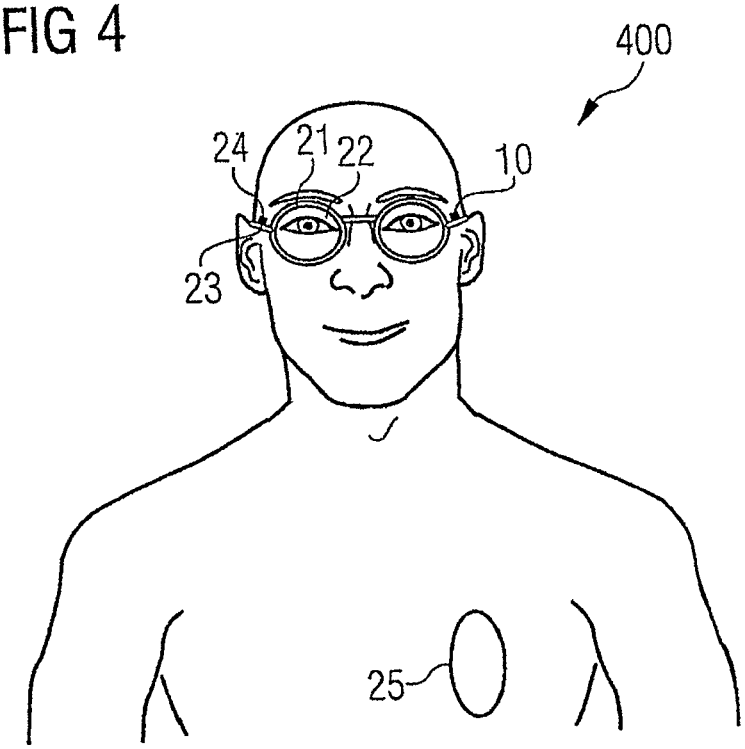
FIG. 4 shows a schematic illustration of a device 400 as per a further exemplary embodiment.

FIG. 1 schematically illustrates a device 100, which includes a control unit 10 and a stimulation unit 11 connected to the control unit 10. The stimulation unit 11 contains a plurality of stimulation elements, which are actuated by the control unit 10. In the present exemplary embodiment, the stimulation unit 11 has two stimulation elements 12 and 13. FIG. 1 furthermore illustrates an eye 14 of a patient.

During the operation of the device 100, the stimulation elements 12 and 13 generate visual stimulation signals 15 and 16, which are received by the patient via one or both eyes 14 and which are transmitted to neuron populations in the brain via the optic nerves. In the process, the control unit 10 actuates the stimulation elements 12 and 13 such that the visual stimulation signals 15 and 16 are generated, for example, in a time-offset fashion.

In a refinement of this embodiment, instead of a time-offset application of the visual stimulation signals 15 and 16, these can also be applied with different phases or different polarities. Furthermore, mixed forms are also feasible, i.e. the visual stimulation signals 15 and 16 can e.g. be offset in time and have different polarities. The device 100 can be developed such that it can be used, for example, to carry out only one of the aforementioned stimulation variants, or the device 100 can alternatively be developed such that it can be used to carry out a plurality of the aforementioned stimulation variants.

The visual stimulation signals 15 and 16 can be based on a luminosity or brightness variation (or a variation of the light intensity or luminosity); these can, for example, be applied as pulses or as sequences of pulses with varying luminosity or brightness. Depending on the refinement of the stimulation unit 11, the visual stimulation signals 15 and 16 can be dispensed as a luminosity modulation of natural visual stimuli, e.g. by means of a homogeneous or segmented pair of transmission glasses, as a modulated visual stimulus occurring in addition to a natural visual stimulus, e.g. by means of a partly transparent pair of light glasses, or as an artificial visual brightness stimulus, e.g. by means of an opaque pair of light glasses. In one embodiment, should the patient take up the visual stimulation signals by both eyes 14, the respective stimulation signals from both eyes 14 can be correlated or coordinated.

The device 100 can more particularly be used for treating neurological or psychiatric diseases such as Parkinson's disease, essential tremor, dystonia, epilepsy, tremor as a result of multiple sclerosis and other pathological tremors, depression, obsessive disorders, Tourette's syndrome, dysfunction after a stroke, tinnitus, sleep disorders, schizophrenia, substance dependences, personality disorders, attention-deficit disorder, attention-deficit hyperactivity disorder, pathological gambling, neuroses, bulimia, burnout syndrome, fibromyalgia, migraine, cluster headache, general headache, neuralgia, ataxia, tic disorder or hypertonia, and the like.

The aforementioned diseases can be caused by a disorder in the bioelectric communication of neural networks connected in specific circuits. Herein, a neuron population continuously generates pathological neuronal activity and possibly a pathological connectivity (network structure) associated therewith. In the process, a large number of neurons form action potentials at the same time, i.e. the involved neurons fire in an overly synchronous fashion. Additionally, the sick neuron population exhibits an oscillatory neuronal activity, i.e. the neurons fire rhythmically. In the case of the aforementioned diseases, the mean frequency of the pathological rhythmic activity of the affected neural networks lies approximately in the range between 1 and 30 Hz, but it can also lie outside of this range. The neurons fire qualitatively differently in healthy humans, e.g. in an uncontrolled fashion.

The visual stimulation signals 15 and 16 generated by the stimulation elements 12 and 13 are developed such that they lead to a resetting, a so-called reset, in the neuron population of the phase of the neuronal activity in the stimulated neurons when they are taken up by the retina and transmitted via the optic nerve to a neuron population with a pathologically synchronous and oscillatory activity. The reset sets the phase of the stimulated neurons to a certain phase value, e.g. 0°, independently of the current phase value. Hence, the phase of the neuronal activity of the pathological neuron population is controlled by means of a targeted stimulation. Furthermore, the plurality of stimulation elements allow the stimulation of the pathological neuron population at different sites. This affords the possibility of resetting the phase of the neuronal activity of the pathological neuron population at different times at the different stimulation sites. As a result, this subdivides the pathological neuron population, the neurons of which were previously active in a synchronous fashion and with the same frequency and phase, into a plurality of subpopulations. Within one subpopulation the neurons are still synchronous and still fire with the same pathological frequency, but each of the subpopulations has the phase in respect of its neuronal activity that was imposed on it by the stimulation stimulus.

Due to the pathological interaction between the neurons, the state with at least two subpopulations, which state was generated by the stimulation, is unstable and the entire neuron population quickly approaches a state of complete desynchronization, in which the neurons fire in an uncorrelated fashion. The desired state, i.e. the complete desynchronization, thus is not available immediately after the application of the stimulation signals via the stimulation unit 11, but usually sets in within a few periods or even within less than one period of the pathological activity.

In the type of stimulation described above, the ultimately desired desynchronization is only made possible by the pathologically increased interaction between the neurons. Hereby, a self-organization process is utilized, which is responsible for the pathological synchronization. The same process brings about a desynchronization following a subdivision of an entire population into subpopulations with different phases. In contrast to this, there would not be desynchronization without a pathologically increased interaction of the neurons.

Moreover, the stimulation with the device 100 can obtain a reorganization of the connectivity of the dysfunctional neural networks and so long-lasting therapeutic effects can be brought about.

FIG. 2 schematically illustrates the visual field 17 of a patient. The space that can be viewed by one eye without eye movements is referred to as the visual field. For the purpose of simplification, the visual field 17 is illustrated in a circular shape in FIG. 2. The visual field typically has a more arched oval form. Here, the precise size and shape of the visual field is subject to individual variations and moreover is age dependent.

By way of example, points in the visual field 17 can be described with the aid of the polar coordinates thereof. The spatial positions of the stimulation elements 12 and 13 in the visual field 17 are illustrated in FIG. 2 in an exemplary fashion. For visualization purposes, one corner of the stimulation elements 12 and 13 is in each case denoted by a vector 18 or 19. In the polar coordinate system, the vectors 18 and 19 can be described by their magnitude and the respective angle $\phi_{18}$ or $\phi_{19}$ that they include with the x-axis.

Different sites in the visual field 17 are imaged on different sites of the retina via the lens of the eye. The different sites of the retina in turn are connected to different neurons in the brain via the optic nerve. This means that the stimulation elements 12 and 13 arranged at different spatial locations can in each case be used to stimulate different neurons. It follows that the stimulation elements 12 and 13, and possibly further stimulation elements, can be spatially arranged in the visual field 17 of the patient such that the stimulation signals taken up by the retina are transmitted to different target areas in the brain. Accordingly, different subpopulations of a pathological neuron population can be stimulated by the stimulation elements 12 and 13 in a targeted fashion, and the phases of these subpopulations can be reset in a time-offset fashion.

The assignment of the regions of the visual field to corresponding regions of the brain is for example described in the article "Visual Field Maps in Human Cortex" by B. A. Wandell, S. O. Dumoulin and A. A. Brewer, published in Neuron 56, October 2007, pages 366 to 383.

In one embodiment, the device 100 can be operated in a so-called "open-loop" mode, in which the control unit 10 actuates the stimulation unit 11 such that the stimulation elements 12 and 13 generate prescribed visual stimulation signals 15 and 16. Moreover, the device 100 can also be developed to form a device 300 shown in FIG. 3, the latter device constituting a so-called "closed-loop" system. In addition to the components known from FIG. 1, the device 300 also contains a measurement unit 20, which provides measurement signals recorded on the patient and transmits said signals to the control unit 10. In a refinement, provision can be made for the control unit 10 to actuate the stimulation unit 11 on the basis of the measurement signals recorded by the measurement unit 20. The measurement unit 20 can involve non-invasive sensors, such as electroencephalography (EEG) electrodes, magnetoencephalography (MEG) sensors, accelerometers, electromyography (EMG) electrodes and sensors for determining blood pressure, respiration or skin resistance. Furthermore, the measurement unit 20 in the form of one or more sensors can be implanted into the body of the patient. By way of example, epicortical, intracortical or subcutaneous electrodes can be used as invasive sensors. In particular, the measurement unit 20 can be used to measure the physiological activity in the stimulated target region or in a region connected therewith.

Various refinements are feasible in respect of the interaction of the control unit 10 with the measurement unit 20. In one embodiment, the control unit 10 can perform a demand-driven stimulation. For this, the control unit 10 detects the presence and/or the development of one or more pathological features on the basis of the measurement signals recorded by the measurement unit 20. For example, the amplitude or the magnitude of the neuronal activity can be measured and compared to a predetermined threshold. The control unit 10 can be developed such that stimulation of one or more target areas is initiated as soon as the prescribed threshold is exceeded. Furthermore, parameters of the visual stimulation signals, such as the strength (amplitude) of the stimulation signals or the frequency of the stimulation or the pauses between the stimulation sequences, can be set by the control unit 10 on the basis of the development of the pathological features. By way of example, one or more thresholds can be prescribed, and if the amplitude or the magnitude of the measurement signals exceeds or drops below a certain threshold the control unit 10 varies a particular parameter of the visual stimulation signals.

In a further embodiment, provision can be made for the measurement signals recorded by the measurement unit 20 to be converted directly or if need be after one or more processing steps into visual stimulation signals and to be applied by the stimulation unit 11. By way of example, the measurement signals, amplified and if need be after mathematical combination (e.g. after mixing the measurement signals) with a time delay and linear and/or nonlinear combination steps, can be fed as control signals into the control inputs of the stimulation elements 12 and 13. Herein, the combination mode is selected such that the pathological neuronal activity is counteracted and the stimulation signals likewise disappear or are at least significantly reduced in strength as the pathological neuronal activity reduces.

FIG. 4 schematically shows a device 400 that constitutes a development of the device 100 shown in FIG. 1. There is no need to implant any component of the device 400, and so the entire device 400 is located outside of the body of the patient. Moreover, the device 400 does not use any signal measured by a sensor for the demand-driven variation of the stimulation. A pair of transmission glasses are used as a stimulation unit 11 in the device 400, which glasses consist of the following components: (i) two rim parts 21, each with one transmission-modulated glasses lens 22 (individual for each eye), (ii) two ear pieces 23, by means of which the glasses are mechanically held behind the ear of the patient, and (iii) the control unit 10, which controls the transmission of the transmission-modulated lenses of the glasses. One of the glasses described further below, e.g. a partly transparent or opaque pair of light glasses, could also be used as a pair of stimulation glasses instead of a pair of transmission glasses. A battery or a rechargeable battery for supplying the electrical components of the device 400 with current can be housed in the control unit 10 or else structurally separately from the control unit 10 in or on the glasses. The glasses can be switched on by the patient by means of an operating unit 24 (e.g. switch-on button and/or control dial). The control dial can be used to set e.g. the maximum stimulation strength. In addition to the aforementioned components, the device 400 can comprise a control medium 25, which for example is connected to the control unit 10 in a telemetric fashion or by means of a connection cable. In the case of a cabled connection, plug-in connections can be used for connection and disconnection.

Furthermore, the device 400 can also comprise an additional control medium (not illustrated) operable by e.g. a medical practitioner, which control medium is connected to the control unit 10 in a telemetric fashion or by means of a connection cable. In the case of a cabled connection, plug-in connections can be used for connection and disconnection.

Moreover, one or more sensors, e.g. EEG electrodes or an accelerometer, can be provided for registering and/or documenting the stimulation success or for the examination by the medical practitioner.

FIGS. 5 to 8 illustrate devices 500, 600, 700 and 800 as exemplary embodiments of the device 300. The devices 500 to 800 in each case comprise a measurement unit, by means of which demand-driven control or feedback of the measurement signals into the stimulation unit can be performed. In this case, the devices 500 and 600 constitute non-invasive variants, while the devices 700 and 800 are partly implanted into the body of the patient. Like the device 400, the devices 500 to 800 comprise a homogeneous or segmented pair of transmission glasses as a stimulation unit. Alternatively, differently developed stimulation units can also be utilized, e.g. the partly transparent or opaque light glasses described further below.

Figure 5:
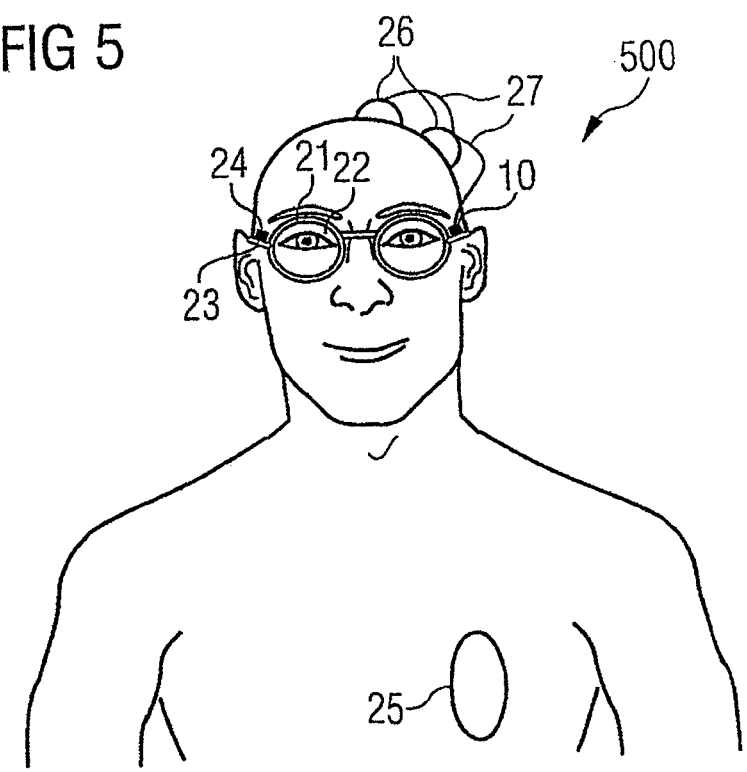
FIG. 5 shows a schematic illustration of a device 500 as per a further exemplary embodiment.

In addition to the above-described components of the device 400, the device 500 illustrated in FIG. 5 comprises epicutaneous, i.e. attached to the skin of the patient, EEG electrodes 26 that are connected to the control unit 10 via connection cables 27. The control unit 10 amplifies the potential difference measured by means of the EEG electrodes 26 and uses said potential difference for actuating the transmission-modulated lenses of the transmission glasses after an optional linear or nonlinear combination. In an alternative embodiment, the EEG electrodes 26 can also be connected wirelessly, i.e. telemetrically, to the control unit 10. Advantageously, the patient is not impeded by connection cables and cannot be caught in e.g. obstacles.

Figure 6:
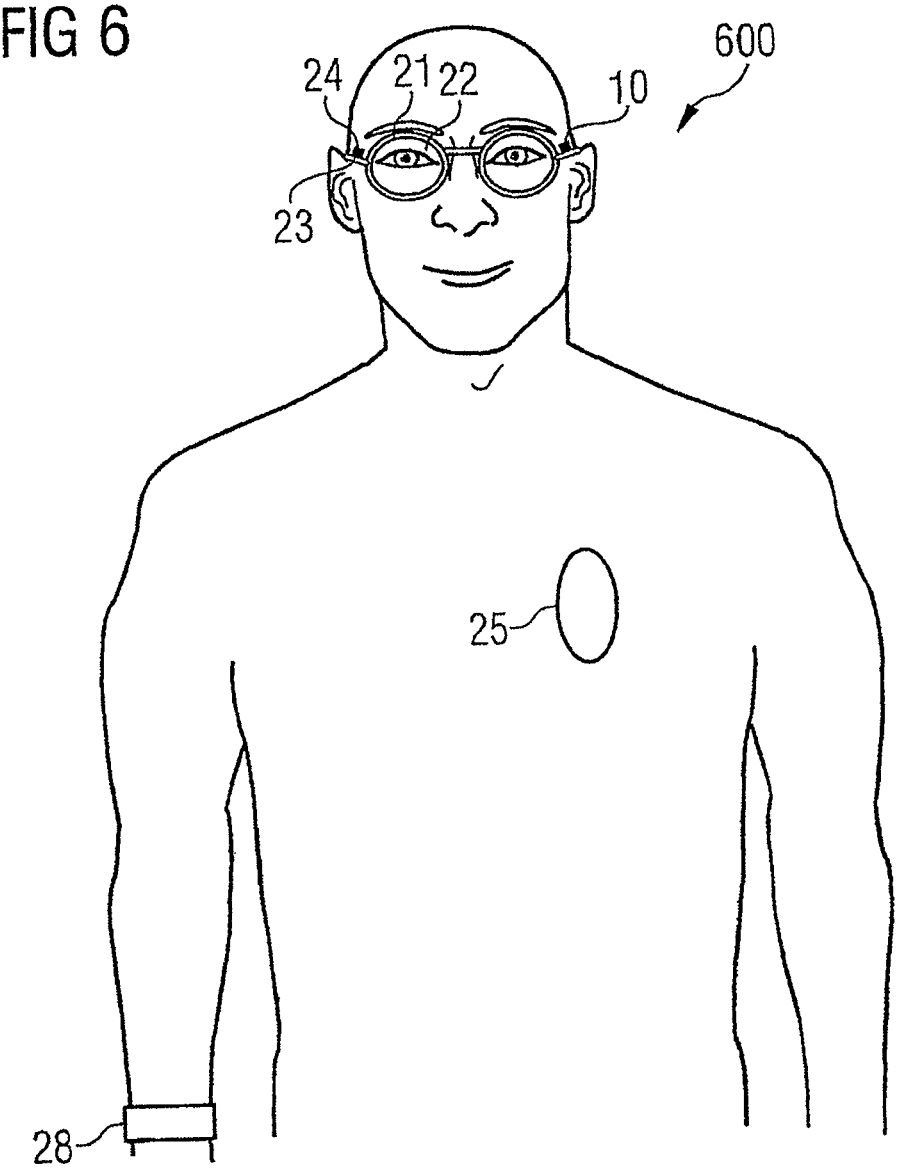
FIG. 6 shows a schematic illustration of a device 600 as per a further exemplary embodiment.

The device 600 illustrated in FIG. 6 has an accelerometer 28 as a measurement unit instead of an EEG electrode. The accelerometer 28 is attached, e.g. like a watch, to a limb of the patient that trembles due to disease. The acceleration signals recorded by the accelerometer 28 are amplified in the control unit 10 and are used for actuating the transmission-modulated lenses of the transmission glasses after an optional linear or nonlinear combination. The accelerometer 28 can be connected to the control unit 10 in a telemetric fashion or by means of a connection cable.

Figure 7:
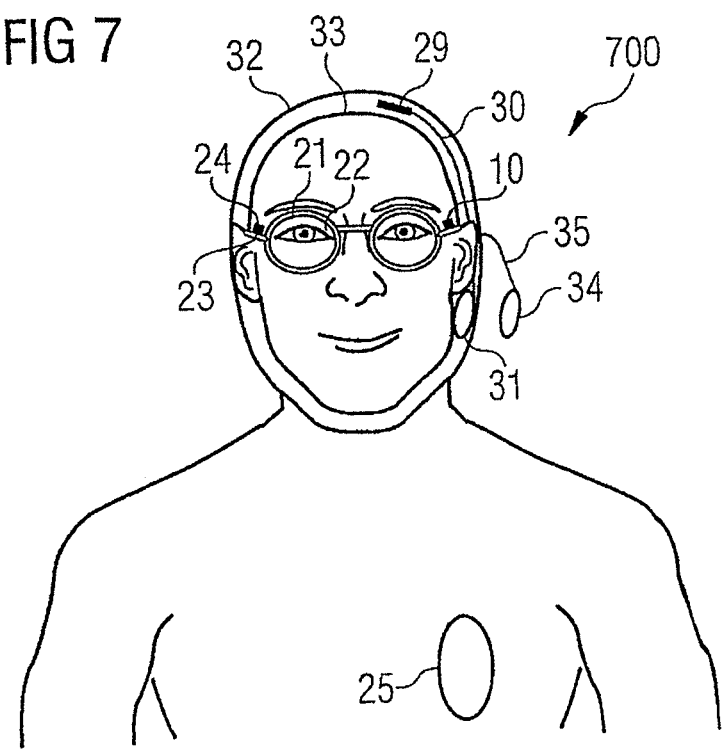
FIG. 7 shows a schematic illustration of a device 700 as per a further exemplary embodiment.

FIG. 7 shows an invasive variant. In the illustrated exemplary embodiment, the device 700 comprises one or more subcutaneously implanted electrodes 29 as a measurement unit, a connection cable 30 and a transmission and reception unit 31, which are implanted into the body of the patient under the scalp 32 and outside of the bony skull 33. Outside of the body of the patient there is a transmission and reception unit 34, which is connected to the control unit 10 via a connection cable 35. The measurement signals recorded by the electrode 29 are transmitted to the control unit 10 via the transmission and reception units 31 and 34, which for example are each implemented as a coil and which allow the wireless and bidirectional transmission of signals and electrical power therebetween. The potential differences measured by the electrode 29 are amplified in the control unit 10 and are used for actuating the transmission-modulated lenses of the transmission glasses after an optional linear or nonlinear combination.

Figure 8:
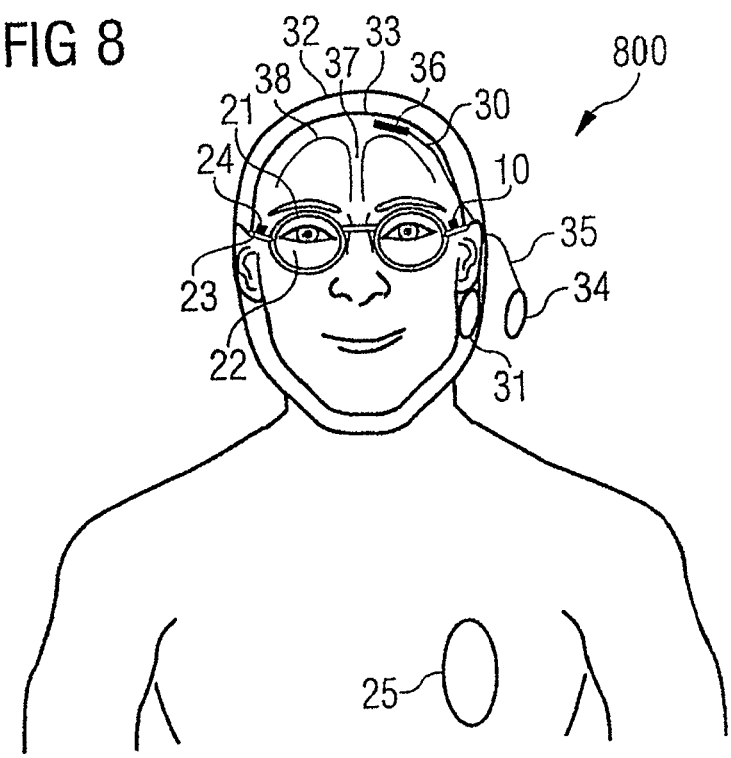
FIG. 8 shows a schematic illustration of a device 800 as per a further exemplary embodiment.

A further invasive variant is illustrated schematically in FIG. 8. One or more epicortically implanted electrodes 36 serve as a measurement unit in the device 800 shown therein. One skilled in the art understands that "epicortical" means "situated on the cerebral cortex". FIG. 8, the space denoted by reference sign 37 between the cerebral cortex 38 and the cranium 33 is shown for illustrative purposes. The cerebral cortex 38 of both hemispheres is shown schematically. The control unit 10 amplifies the potential difference measured by means of the epicortically implanted electrode 36 and uses said potential difference for actuating the transmission-modulated lenses of the transmission glasses after an optional linear or nonlinear combination.

The epicortical electrode 36 shown in FIG. 8 can for example also be replaced by an intracortical electrode (not illustrated).

Figure 9:
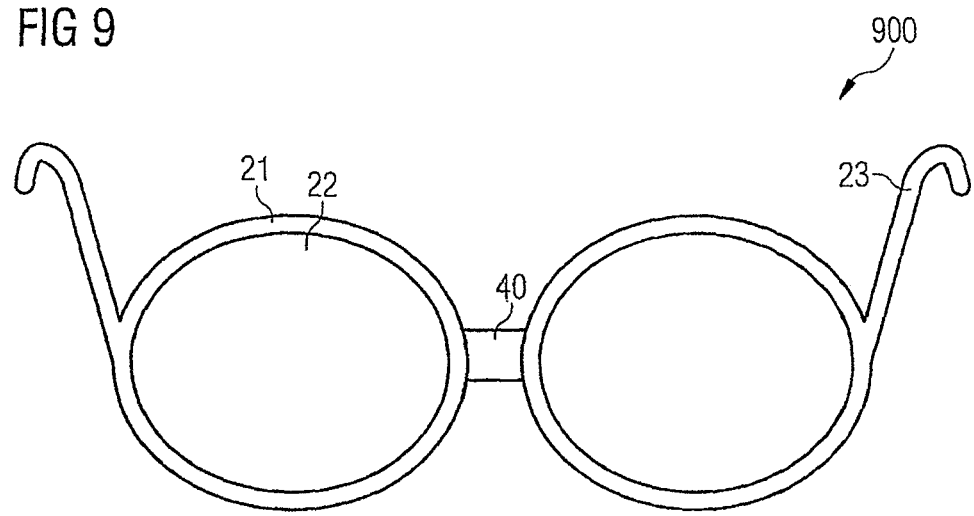
FIG. 9 shows a schematic illustration of a pair of transmission glasses 900 with homogeneous transmission lenses.

FIG. 9 illustrates a pair of transmission glasses 900 with homogeneous transmission lenses 22. The transmission glasses 900 furthermore comprise ear pieces 23 for mechanical attachment to the head of the patient, a web 40, which connects the two transmission lenses 22, and rim parts 21, which hold the transmission lenses 22. The transmission lenses 22 are homogeneous, i.e. they are not subdivided into different segments. The transmission of the right and the left transmission lens 22 can be controlled separately, i.e. the transmission lenses 22 can be used as stimulation elements 12 and 13 within the scope of the device 100. The two eyes of the patient can each be stimulated with different visual stimuli by means of the transmission glasses 900.

Figure 10:
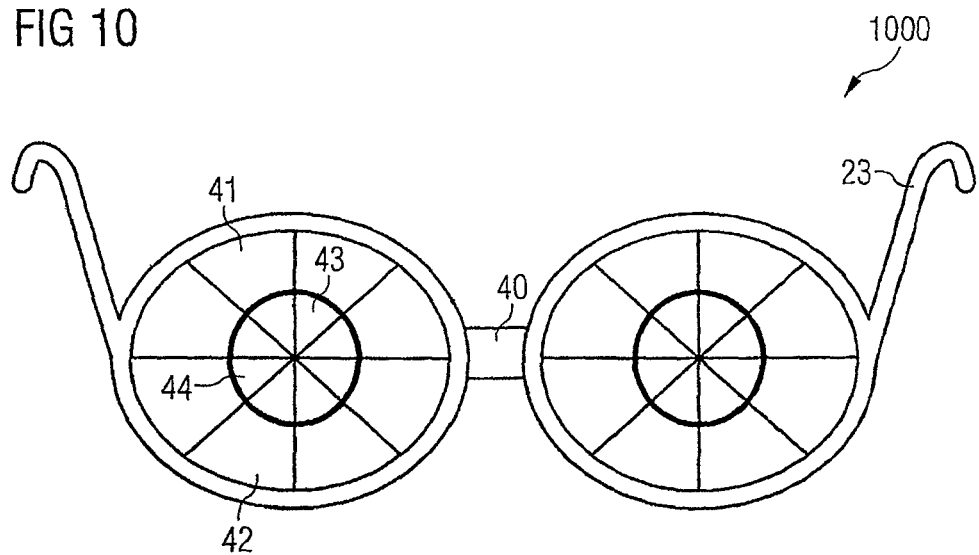
FIG. 10 shows a schematic illustration of a pair of transmission glasses 1000 with segmented transmission lenses.

FIG. 10 illustrates a pair of transmission glasses 1000 with segmented transmission lenses 22. The transmission lenses 22 are respectively subdivided into different segments, the transmission of which can be controlled separately. By way of example, the segmentation can be radial and/or circular (both are shown in FIG. 10). The embodiment shown in FIG. 10 of a pair of segmented transmission glasses should merely be understood as being exemplary. The number of segments and the geometric shapes of the individual segments can be selected such that they differ therefrom.

The segments of the transmission glasses 1000 correspond to the stimulation elements shown in FIG. 1. Four of the segments with the reference signs 41, 42, 43 and 44 are labeled in FIG. 10.

The segments 41 to 44 are provided below to explain in an exemplary fashion as to how a time-offset reset of the phase of subpopulations of a pathologically synchronous and oscillatory neuron population can achieve a desynchronization of the entire neuron population. The segments 41 to 44 have been selected such that the visual stimulation signals generated thereby are each preferably taken up by a particular part of the retina of the patient, from where the stimulation signals are transmitted to certain regions of the brain such that the above-described subdivision of a pathological neuron population into subpopulations is made possible. In order for subpopulations with different phases to be formed, the visual stimulation signals from the segments 41 to 44 can for example be generated with a time offset. A phase-offset generation of the stimulation signals is equivalent to the time-offset generation of the visual stimulation signals, which phase-offset generation of the stimulation signals in end effect likewise leads to a time-offset resetting of the phases of the different subpopulations.

Figure 11:
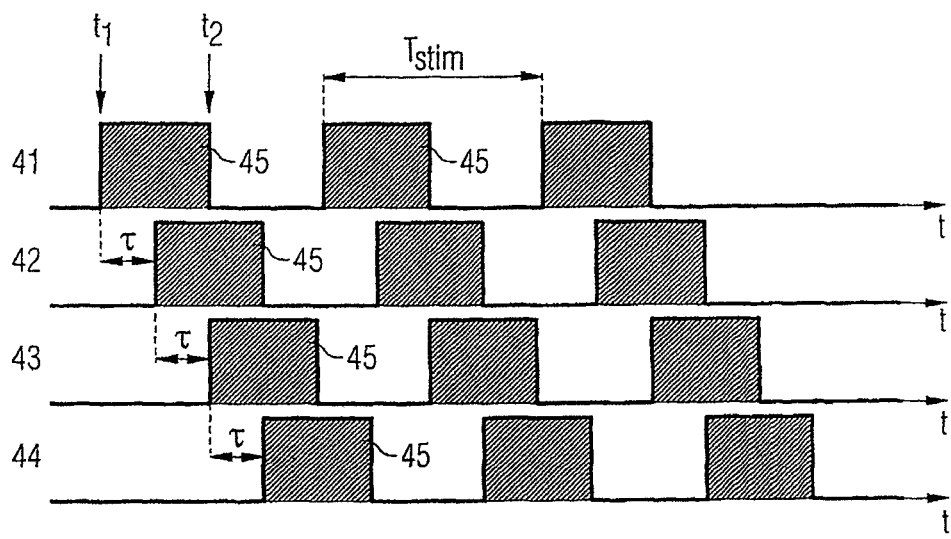
FIG. 11 shows a schematic illustration of visual stimulation signals generated by means of a plurality of stimulation elements.

A stimulation method that is suitable for the above-described purposes and can, for example, be performed by one of the devices 100 to 800 is illustrated schematically in FIG. 11. FIG. 11 plots, one below the other, the visual stimulation signals 45 applied by means of the segments 41 to 44 over time t. In the exemplary embodiment shown in FIG. 11, the assumption is made that only the segments 41 to 44 of the transmission glasses 1000 generate visual stimulation signals 45, i.e. the transmission of these segments only is modulated by the control unit 10. It goes without saying that this should only be understood in an exemplary fashion. Different segments can be used in alternative refinements in order to generate the visual stimulation signals instead of the segments 41 to 44. It is possible that, like in FIG. 11, use is only made of a selection of the segments of the transmission glasses 1000 for the stimulation, or else use can be made of all segments.

In the method illustrated in FIG. 11, each of the segments 41 to 44 periodically applies the visual stimulation signal 45. In the present example, the stimulation signal 45 is applied three times per segment 41 to 44. Alternatively, the stimulation signal 45 could for example also be repeated one to fifteen times in each sequence. The frequency $f_{stim}=1/T_{stim}$, at which the visual stimulation signals 45 are repeated per segment 41 to 44, can lie in the range between 1 and 30 Hz and more particularly in the range between 5 and 20 Hz, but it can also assume smaller or greater values. Such sequences of visual stimulation signals 45 are suitable for resetting the neuronal phase of a stimulated pathological subpopulation of neurons.

In the exemplary embodiment, the frequency $f_{stim}$ can lie in the vicinity of the mean frequency of the pathologically rhythmic activity of the target network. In the case of neurological and psychiatric diseases, the mean frequency typically lies in the range between 1 and 30 Hz, but it can also lie outside of this range. It should be noted herein that the frequency at which the pathological neurons fire synchronously is usually not constant, but can by all means have variations and moreover has individual deviations in each patient.

The mean peak frequency of the pathological rhythmic activity of the patient can for example be determined in order to calculate the frequency $f_{stim}$. This peak frequency can then be used as stimulation frequency $f_{stim}$, or else be varied, for example in a range between $f_{stim}-3$ Hz and $f_{stim}+3$ Hz. However, alternatively it is also possible for a frequency $f_{stim}$ to be selected in the range between 1 and 30 Hz without a preceding measurement and this frequency can for example be varied during the stimulation until the frequency $f_{stim}$ is found, by means of which the best stimulation successes can be obtained. As a further alternative, a known value found in the literature for the respective disease can be used for the stimulation frequency $f_{stim}$. It should be understood that if necessary, this value can still be varied until, for example, optimum stimulation results are obtained.

The structure of an individual visual stimulation signal 45 should be explained hereinbelow on the basis of the first stimulation signal 45 generated by the segment 41. Herein, the segment 41 is actuated by the control unit 10 at the time $t_1$ such that the transmission, i.e. the transparency of the segment 41 with respect to light, is minimized. At the time $t_2$ the control unit 10 switches the transmission of the segment 41 to the maximum value. In other words, this means that the segment 41 becomes less transparent when stimulation is performed. Accordingly, during the stimulation, the patient perceives a reduced brightness of the surrounding light in the region of the segment 41.

As an alternative, it is also possible for the transmission of the segment 41 to be switched to the maximum at the time $t_1$ and to the minimum at the time $t_2$, and so the segment 41 becomes more transparent during the stimulation.

In principle it is feasible for 100% to be selected as maximum transmission, i.e. none of the surrounding light is attenuated by the respective segment in this case. However, one skilled in the art understands that it is often not possible to achieve such a high transmission due to technical limitations, and so smaller transmission values in the range between 60% and 100% can be selected for the maximum transmission. The minimum transmission can assume a value in the range between 0% and 30%. However, stimulation successes can also be obtained with transmission values that lie outside of the specified ranges.

The duration of a stimulation signal 45, i.e. the period of time between the times $t_1$ and $t_2$, can for example be $T_{stim}/2$. In this case, the period of time during which stimulation takes place and the subsequent stimulation pause have the same length. However, other stimulation durations can also be selected, for example in the range between $T_{stim}/2-T_{stim}/10$ and $T_{stim}/2+T_{stim}/10$. Other stimulation times are also possible and can for example be determined experimentally.

According to the refinement shown in FIG. 11, the visual stimulation signals 45 are dispensed by the individual segments 41 to 44 of the transmission glasses 1000, with a time delay between the individual segments 41 to 44. By way of example, the beginning of temporally successive visual stimulation signals 45 applied by different segments 41 to 44 can be offset by a time τ.

In the case of N stimulation elements or segments used for the stimulation, the time delay τ between two respectively successive stimulation signals 45 can for example lie in the vicinity of an N-th of the period $T_{stim}=1/f_{stim}$. In the exemplary embodiment (N=4) shown in FIG. 11, the time delay τ correspondingly is $T_{stim}/4$. There can be a certain amount of deviation from the specification that the time delay τ between two respectively successive stimulation signals 45 is $T_{stim}/N$. By way of example, there can be a deviation of up to ±10%, ±20% or ±30% from the value $T_{stim}/N$ for the time delay τ.

Stimulation successes were still obtained in the case of such a deviation, i.e. a desynchronizing effect could still be observed.

The rectangular shape of the individual pulses 45 illustrated in FIG. 11 represents an ideal shape. There are deviations from the ideal rectangular shape depending on the quality of the electronics generating the individual pulses 45 and the transmission lenses 22.

Figure 12:
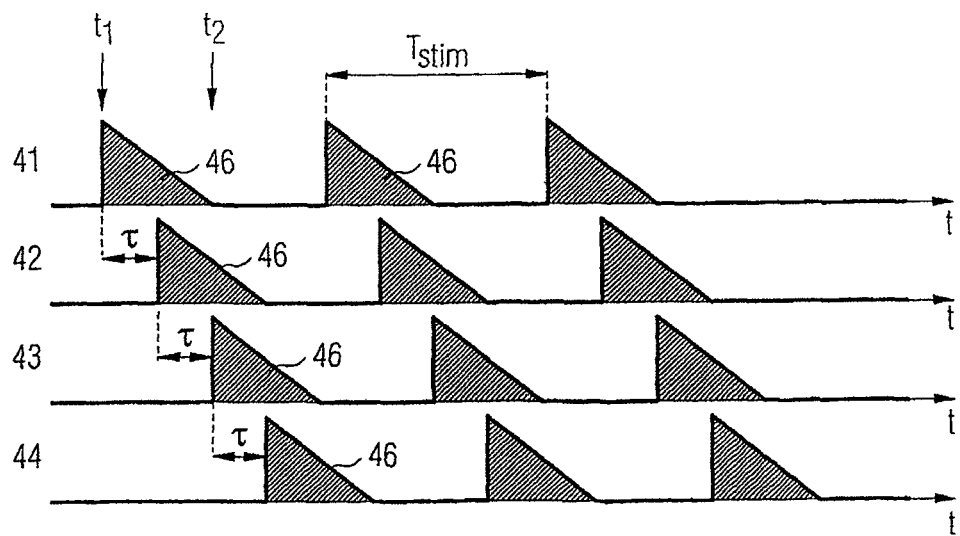
FIG. 12 shows a schematic illustration of visual stimulation signals generated by means of a plurality of stimulation elements.
Figure 13:
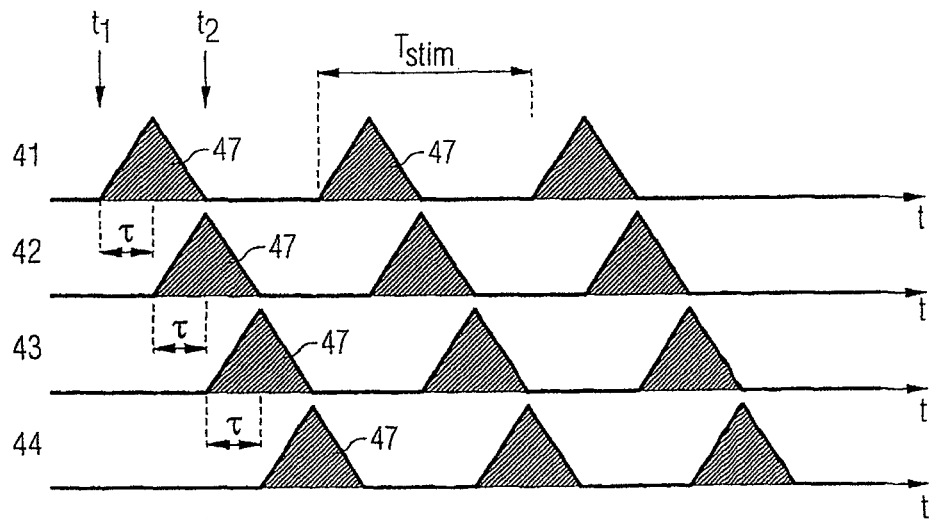
FIG. 13 shows a schematic illustration of visual stimulation signals generated by means of a plurality of stimulation elements.
Figure 14:
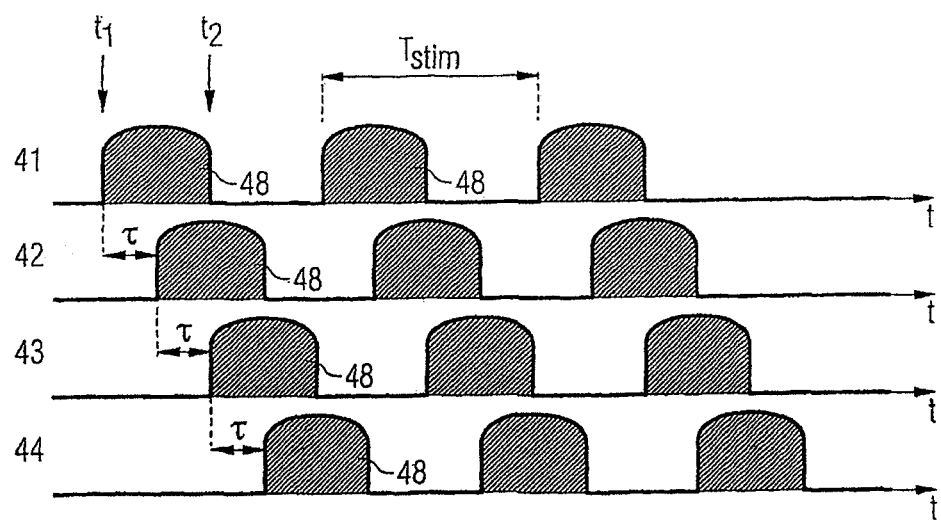
FIG. 14 shows a schematic illustration of visual stimulation signals generated by means of a plurality of stimulation elements.

Alternatively, instead of rectangular stimulation signals 45, the control unit 10 can, for example, also generate differently formed stimulation signals, as are illustrated in an exemplary fashion in FIGS. 12 to 14. FIG. 12 shows triangular visual stimulation signals 46. By way of example, a switch to minimum transmission is made at the time $t_1$, and the transmission rises continuously to the maximum value up until the time $t_2$. Alternatively, provision can be made for the transmission to be at a maximum at the beginning of the stimulation signal 46 and to subsequently fall to the minimum value.

FIG. 13 shows triangular visual stimulation signals 47 with a rising and a falling edge. Here, the transmission is for example increased starting at the time $t_1$ and reduced again up until the time $t_2$ after reaching the maximum.

Furthermore, in a refinement of the exemplary embodiment, provision can be made for the rising and falling edges of the visual stimulation signals to be "rounded" (for example in an exponential fashion). This is shown in FIG. 14 with the help of rounded rectangular visual stimulation signals 48. Moreover, the stimulation signals can also be replaced by a simple sinusoidal shape.

The above-described signal shapes and the parameters thereof should only be understood as being exemplary. It is by all means possible to deviate from the aforementioned signal shapes and the parameters thereof within the spirit and scope of the application.

It should be understood that there can be various deviations from the strictly periodic stimulation pattern shown in FIGS. 11 to 14. By way of example, the time delay τ between two successive stimulation signals 45, 46, 47 or 48 need not necessarily always to be of the same magnitude. Provision can be made for the time separations between the individual stimulation signals 45, 46, 47 or 48 to be selected such that they differ. Furthermore, the delay times can also be varied during the treatment of a patient. The delay times can also be adjusted in respect of the physiological signal run times.

Furthermore, pauses can be provided during the application of the stimulation signals 45, 46, 47 or 48, during which pauses there is no stimulation. The pauses can be selected to have any duration and more particularly are an integer multiple of the period $T_{stim}$. The pauses can be held after any number of stimulations. For example, a stimulation can be performed over N successive periods of length $T_{stim}$, and there can subsequently be a stimulation pause over M periods of length $T_{stim}$, wherein N and M are small natural numbers, for example in the range between 1 and 15. This scheme can be either continued periodically or modified stochastically and/or deterministically, e.g. chaotically.

A further option for deviating from the strictly periodic stimulation pattern shown in FIGS. 11 to 14 includes stochastic or deterministic or mixed stochastic-deterministic variation of the time separations between successive stimulation signals 45, 46, 47 or 48 in each segment 41 to 44.

In an additional refinement, the order in which the segments 41 to 44 apply the stimulation signals 45, 46, 47 or 48 can be varied during each period $T_{stim}$ (or during other time steps). This variation can be stochastic or deterministic or mixed stochastic-deterministic.

Furthermore, it is also possible for only a certain number of the segments 41 to 44 to be used for the stimulation during each period $T_{stim}$ (or during another time interval) and the segments involved in the stimulation may be varied in each time interval. This variation can also be stochastic or deterministic or mixed stochastic-deterministic.

Visual stimulation signals with other signal shapes can also be used instead of the pulse-shaped and mutually time-offset visual stimulation signals 45 to 48 shown in FIGS. 11 to 14. By way of example, each of the segments 41 to 44 can generate an (e.g. continuous) sinusoidal signal, wherein the phases of the sinusoidal signals generated from different segments 41 to 44 are shifted with respect to one another.

The mean frequency of the sinusoidal signals can in this case be equal. The phase shifts between the individual sinusoidal signals can either be prescribed (for example, the phase shift between respectively two of N stimulation signals can be $T_{stim}/N$) or the phase shifts can be varied e.g. chaotically and/or stochastically. Furthermore, the visual stimulation signals can have different polarities. By way of example, in the case of a sinusoidal signal as the stimulation signal, the sinusoidal signal of two segments can be applied simultaneously but with opposite polarity (corresponding to a phase shift of 180°).

Furthermore, each of the segments 41 to 44 can in each case apply a sinusoidal signal at a different frequency. By way of example, one of the segments can apply a sinusoidal signal at 5 Hz, and the other three segments can apply sinusoidal signals at 4 Hz, 3 Hz and 2 Hz (i.e. in the case of a pair of transmission glasses, the transmission of the respective segment 41 to 44 changes with the corresponding frequency). Use can also be made of other (oscillating) signal shapes, e.g. rectangular signals, with the corresponding base frequency instead of sinusoidal signals. The signals need not be applied with a time offset; rather, the segments 41 to 44 can also for example generate the stimulation signals at the same time. The stimulation signals can be applied continuously over a relatively long period of time; however, there can also be pauses during the application.

The application of visual stimulation signals with different frequencies does not necessarily lead to a rapid resetting of the phase of the neuronal activity in the respective stimulated subpopulations, but the stimulation using these signals over a certain period of time forces a particular phase onto the respectively stimulated subpopulations, which phase depends on the respective stimulation frequency. Ultimately, this also leads to a desynchronization of the entire neuron population.

Furthermore, it is noted that all stimulation forms described above can also be performed in a "closed-loop" mode. Moreover, it is feasible for the stimulation to be started by the patient, for example by means of a telemetric activation. In this case, the patient can activate the stimulation for a prescribed period of time of e.g. 5 minutes or the patient can independently start and stop the stimulation.

Figure 15:
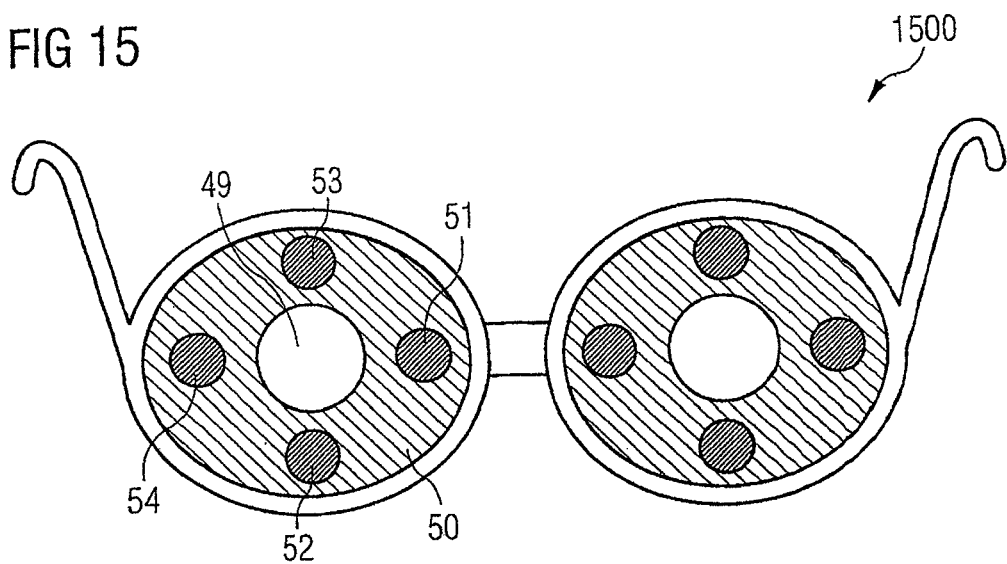
FIG. 15 shows a schematic illustration of a partly transparent pair of light glasses 1500.

FIG. 15 schematically illustrates a pair of partly transparent light glasses 1500 as a further embodiment of the stimulation unit 11. In the case of the partly transparent light glasses 1500, use is not made of a lens with a variable transmission. Rather, only a part 49 of each of the glasses lenses is transparent, whilst the remaining part 50 of the glasses lenses is opaque. A light source is arranged at least one location in each glasses lens. The light source can be e.g. a light-emitting diode or a fiber-glass cable, which transmits e.g. the light from a light-emitting diode or another light means attached at a different site to this site on the glasses lens. The light glasses 1500 shown in FIG. 15 have four light sources 51, 52, 53 and 54 for each glasses lens. However, the light glasses 1500 can also comprise any other number of light sources, which can be arranged in any geometry. Furthermore, the transparent part 49 can also have a different design than illustrated in FIG. 15.

The patient can only see through the transparent part 49 of the glasses lenses. If this part is small compared to the entire glasses lens, the patient is forced to keep their eyes at a constant position relative to the glasses. The light sources 51 to 54 only stimulate the retina of the patient and do not visually stimulate an observer on the other side of the glasses. The various light sources 51 to 54 for example stimulate particular portions of the retina of the patient. The interspace between the edge of the glasses and the face can be closed off in an opaque fashion (not illustrated).

Figure 16:
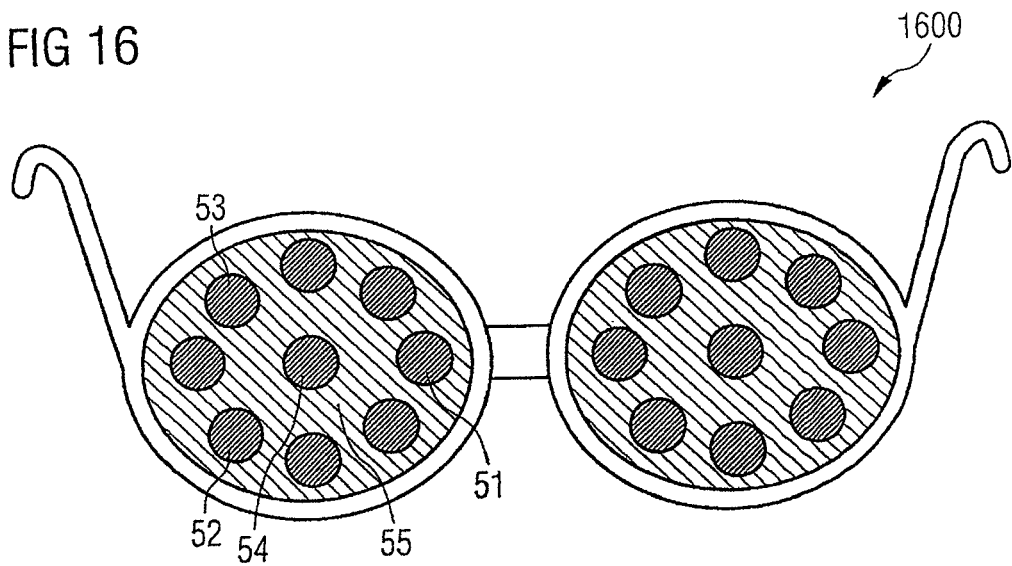
FIG. 16 shows a schematic illustration of an opaque pair of light glasses 1600.

FIG. 16 schematically illustrates a pair of opaque light glasses 1600 as a further embodiment of the stimulation unit 11. In the case of the opaque light glasses 1600, the glasses lens 55 is completely opaque. A light source is affixed at least one location in each of the glasses lenses 55. The light sources can be formed just like in the partly transparent light glasses 1500, that is to say as e.g. light-emitting diodes or fiber-glass cables. Each of the glasses lenses has nine light sources in the example shown in FIG. 16. Four of these light sources are denoted by the reference signs 51 to 54. However, the light glasses 1600 can also have any other number of light sources, which can be arranged in any fashion.

The patient cannot see through the glasses lenses, but is only visually stimulated by the light sources. As in the case of the partly transparent light glasses 1500, the light sources only stimulate the retina of the patient. The various light sources stimulate particular portions of the retina of the patient. The interspace between the edge of the glasses and the face can be closed off in an opaque fashion (not illustrated).

The opaque light glasses 1600 can contain a fixation target, which the patient can comfortably fixate on (e.g. without blinding effects). The instruction to fixate on the fixation target during the therapy prevents the patient from following the different illuminating light sources with eye pursuit movements. In the latter case, it would mainly be the central part of the retina (the fovea) that is stimulated, whereas a fixation target allows stimulation of the different parts of the retina.

Figure 17:
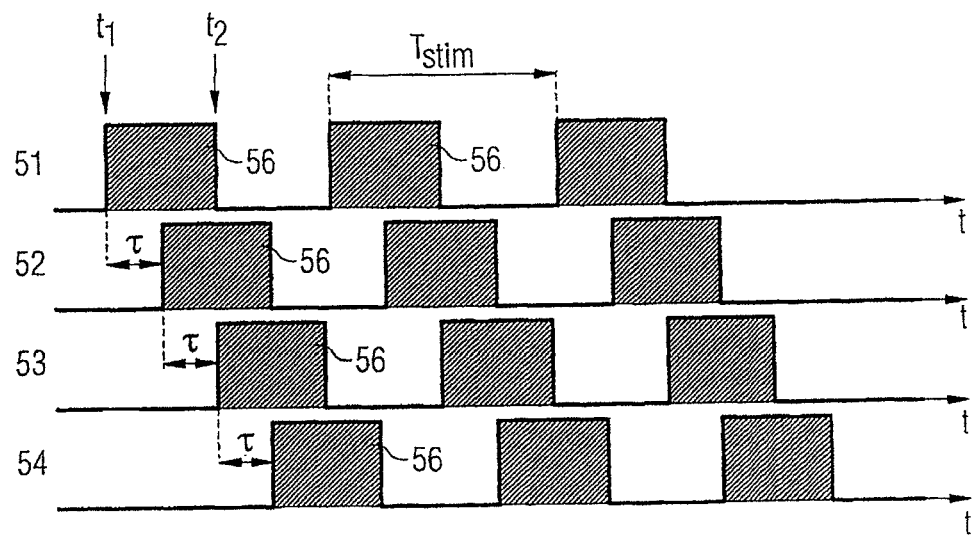
FIG. 17 shows a schematic illustration of visual stimulation signals generated by means of a plurality of stimulation elements.

A stimulation method, which can, for example, be carried out with the light glasses 1500 or 1600, is illustrated schematically in FIG. 17. FIG. 17 plots, one below the other, the visual stimulation signals 56 applied by the light sources 51 to 54 of the light glasses 1500 or 1600 over time t.

The method illustrated in FIG. 17 substantially corresponds to the method shown in FIG. 11 for the transmission glasses 1000. In the method illustrated in FIG. 17, each of the light sources 51 to 54 periodically applies the visual stimulation signal 56. The frequency $f_{stim}=1/T_{stim}$ at which the visual stimulation signals 56 are repeated per light source 51 to 54 can lie in the range between 1 and 30 Hz and more particularly in the range between 5 and 20 Hz, but it can also assume smaller or greater values.

FIG. 17 only illustrates the stimulation method for four light sources 51 to 54 for the sake of simplicity. However, it should be appreciated that this method can correspondingly be expanded to any number of light sources.

When generating the visual stimulation signals 56 by means of light sources, the relevant light source is typically switched on at the time $t_1$ and switched off at the time $t_2$. The maximum amplitude (brightness) of the individual light stimuli for example lies in a range between 1 and 20 cd/m². It is also possible for smaller brightness values to be used during the stimulation, i.e. during the period of time between $t_1$ and $t_2$.

It should be understood that all refinements described in conjunction with FIGS. 11 to 14 may also be correspondingly transferred to the stimulation by means of the light glasses 1500 or 1600.

By way of example, a pair of video glasses can also be used to apply the visual stimulation signals as a further alternative to the transmission glasses 900 and 1000 and the light glasses 1500 and 1600. In this type of stimulation, a video image or a video film is projected into the visual field of the patient. The video image or the video film can be subdivided into segments, and the brightness of the individual segments can be varied analogously to the above-described stimulation methods. The video image or the video film can either be produced in advance, or one or more video cameras can be attached to the glasses, by means of which cameras the video image or the video film is recorded.

Figure 18:
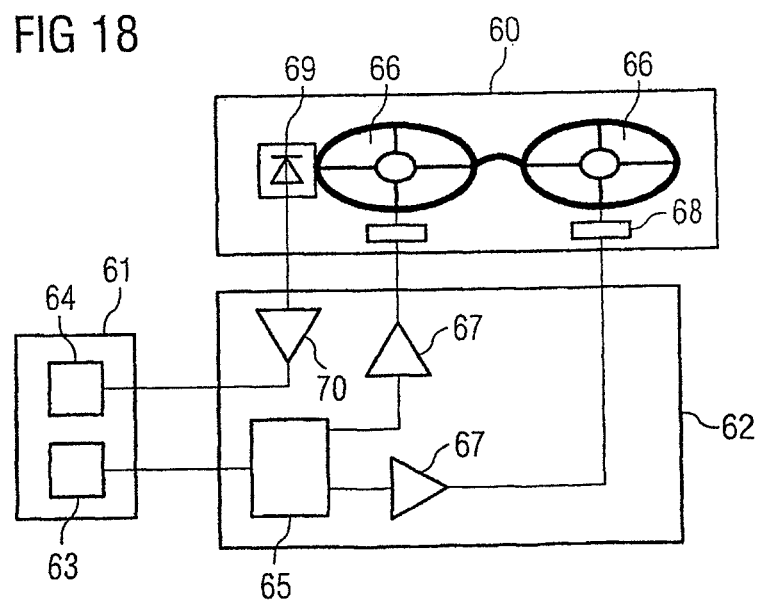
FIG. 18 shows a schematic illustration of a segmented pair of transmission glasses with actuation electronics.

FIG. 18 schematically illustrates a pair of segmented transmission glasses 60 with actuation electronics as a further exemplary embodiment. In the exemplary embodiment, the transmission lenses have been implemented using liquid crystal display (LCD) technology. The actuation electronics consist of an input module 61 and an actuation module 62. The input module 61 has an input 63 and an output 64, by means of which the transmission glasses 60 can be connected to the control unit 10. An input signal fed into the input 63 is transmitted to an adjustment unit 65, which sets the transmission of the individual segments 66 of the transmission glasses 60. The levels of the control signals generated by the adjustment unit 65 are still amplified in advance to suitable values by amplifier units 67. The transmission of each segment 66 of the transmission glasses 60 can be controlled individually. For this purpose, each of the segments 66 has been provided with a connector 68, by means of which the respective control signal can be fed in.

Additionally, the transmission glasses 60 can comprise a photodiode 69, which can for example be integrated into a glasses lens. The photodiode 69 can be used to detect the amplitude (brightness) of the surrounding light in order to be able to set the maximum modulation amplitude, i.e. the contrast, of the transmission glasses 60 with the aid of this value. The signal generated by the photodiode 69 is preamplified by an amplifier unit 70 and provided at the output 64.

Figure 19:
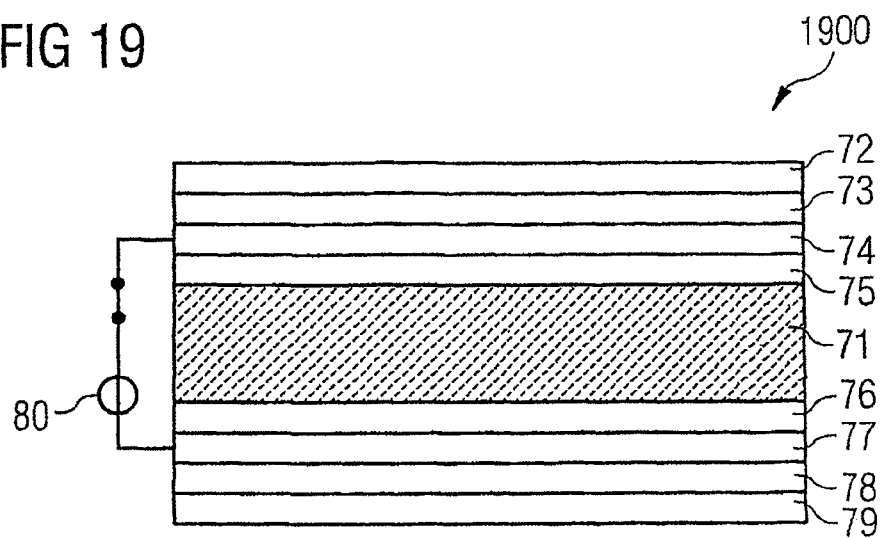
FIG. 19 shows a schematic illustration of a cross section through an LCD transmission glass.

FIG. 19 schematically shows a cross section through an LCD transmission glass 1900. The LCD transmission glass 1900 includes a twisted nematic (TN) liquid crystal 71, which is inserted into a stack of active and passive layers. As illustrated in FIG. 19, a transparent front-side glass plate 72, a polarizer 73, a segmented, transparent and electrically conductive layer 74 and an alignment layer 75 are arranged on the one side of the TN liquid crystal 71. Arranged on the other side of the TN liquid crystal 71 are an alignment layer 76, a continuous, transparent and electrically conductive layer 77, a polarizer 78 and a transparent rear-side glass plate 79. The distance between the two electrically conductive layers 74 and 77 is typically between 2 and 20 µm. In order to maintain suitable distances between the individual layers, spacers can be used, which consist of e.g. small glass spheres or rods.

A voltage source 80 can be used to apply a voltage between the two electrically conductive layers 74 and 77, which voltage can be used to adjust the transmission of the surrounding light incident on the LCD transmission glass 1900. The polarization directions of the polarizers 73 and 78 can be aligned to be perpendicular with respect to one another. The unpolarized surrounding light is linearly polarized by the polarizer 73.

The TN liquid crystal 71 brings about a 90° rotation of the linearly polarized light such that the polarization direction of the light thereafter corresponds to the polarization direction of the polarizer 78 and so said light can pass through the latter without a loss of intensity. The electrical field generated by the voltage source 80 changes the rotation of the polarization brought about by the TN liquid crystal 71, which results in a change in the optical transmission.

It should be appreciated that the above-described principle for varying the transmission can be modified in various ways. For example, two "guest-host" liquid-crystal cells can be aligned to be perpendicular with respect to one another, as a result of which both directions of the polarized light are absorbed in the switched-off state and high contrast ratios are made possible without polarizers. The transparent state is attained by applying a suitable voltage that aligns the polarization directions of the two liquid-crystal cells in the same direction.

In addition to the aforementioned TN liquid crystal it is also possible for other types of liquid crystals to be used as the liquid crystal, for example so-called "polymer stabilized cholesteric textured" or "electrically commanded surface" liquid crystals are suitable.

By way of example, indium tin oxide (ITO) can be used for producing the electrically conductive layers 74 and 77. Indium tin oxide can be applied to the TN liquid crystal 71 by means of e.g. electron beam evaporation, physical vapor deposition or sputtering.

Figure 20:
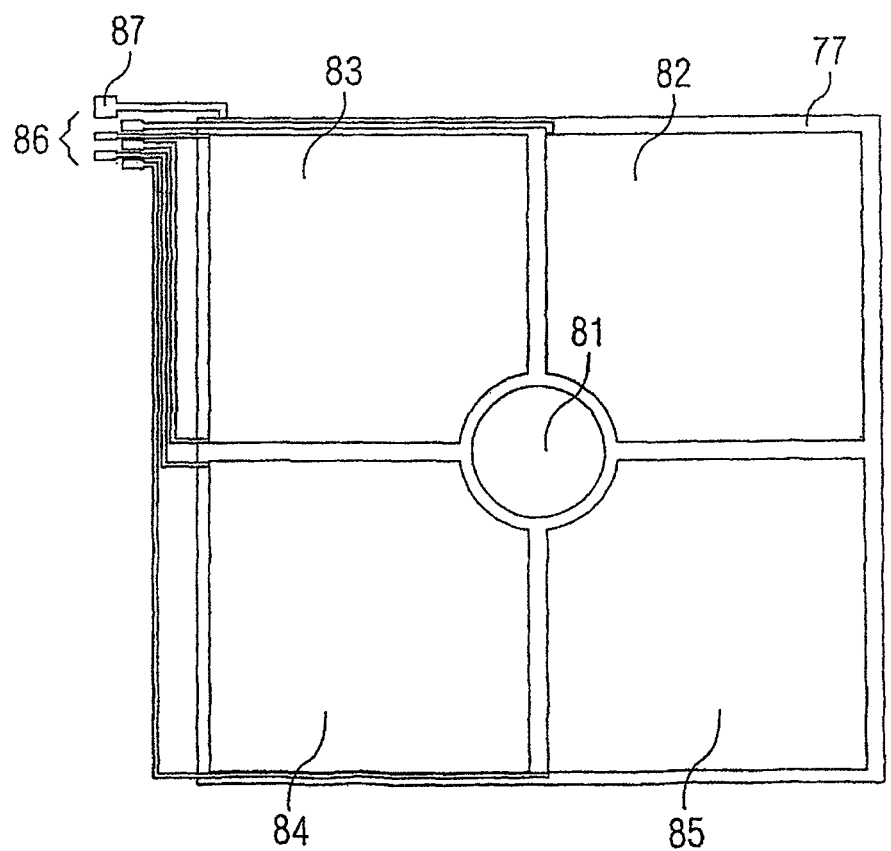
FIG. 20 shows a schematic illustration of a segmented electrically conductive layer.

It is noted that in order to have the individual segments of the transmission glasses actuated separately, one of the two electrically conductive layers 74 and 77 is segmented. FIG. 20 illustrates a segmentation of the electrically conductive layer 74 in an exemplary fashion. In the exemplary embodiment, the electrically conductive layer 74 includes five segments 81 to 85, which are electrically insulated from one another. Each of the segments 81 to 85 has its own connector 86 assigned to it, by means of which the individual segments 81 to 85 can each be actuated separately. The electrically conductive layer 77 likewise has its own connector 87. In order to actuate one of the segments 81 to 85, a suitable voltage is applied between the respective connector 86 and the connector 87.

Figure 21:
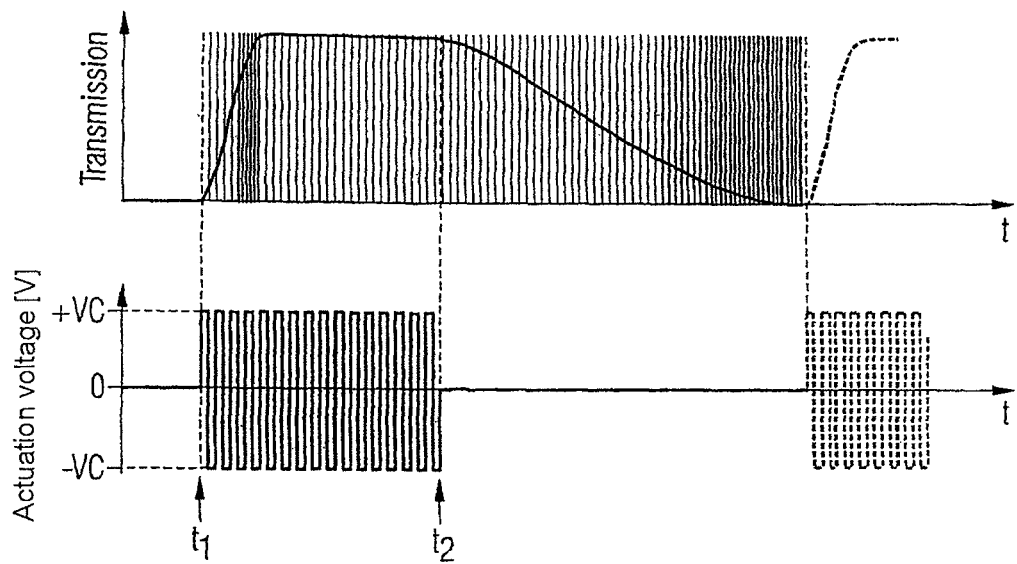
FIG. 21 shows a schematic illustration of the actuation and transmission property of a segment of a pair of transmission glasses.

FIG. 21 illustrates the actuation of one of the segments 81 to 85 and the transmission property of the corresponding segment as a response to the applied actuation voltage. FIG. 21 shows that the transmission is started to be ramped up to the maximum value at the time $t_1$, and the transmission is again reduced to the minimum value at the time $t_2$. No direct current is applied to the electrically conductive layers 74 and 77 in the switched-on state, i.e. between the times $t_1$ and $t_2$; rather, the actuation voltage is switched to and fro between the voltage values +VC and −VC at a frequency in the range between 10 Hz and 5 kHz. Here, the temporal average of the applied voltage is 0 V. Applying the amplitude-modulated voltage prevents a migration of ions, which would destroy the LC cell in an irreversible fashion. In order to stop ions from penetrating the TN liquid crystal 71, the electrically conductive layers 74 and 77 can furthermore be provided with protective layers, which can consist of e.g. silicon dioxide.

The maximum contrast of the segments 81 to 85 is generated by means of the voltage +VC/−VC. The transmission/extinction can be adjusted by modulating the voltage (V<VC) applied to the electrically conductive layers 74 and 77, and variable grayscale values can be generated.

Figure 22:
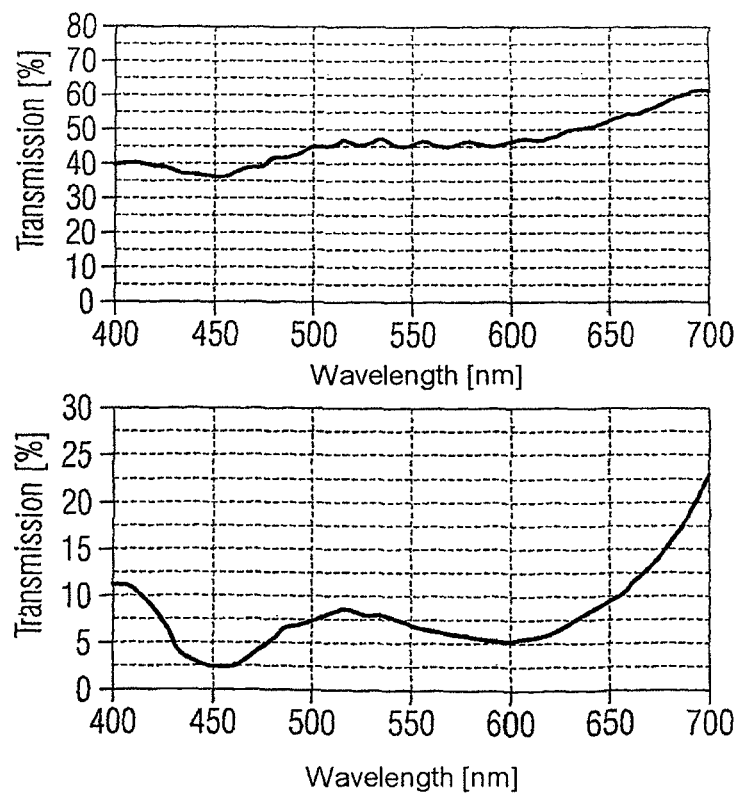
FIG. 22 shows an illustration of a transmission spectrum of a pair of transmission glasses.

FIG. 22 illustrates in an exemplary fashion the transmission spectrum of two "guest-host" liquid-crystal cells aligned perpendicular with respect to one another. In the present example, the thickness of the liquid-crystal layer is 4 μm. The upper image shows the "guest-host" liquid-crystal cells in the switched-on state with maximum transmission, and the lower image in the switched-off state with minimum transmission.

The refinements of a pair of transmission glasses shown in FIGS. 18 to 22 should only be understood as being exemplary. A pair of transmission glasses for implementing the stimulation unit 11 shown in FIG. 1 can also have other refinement features.

Figure 23:
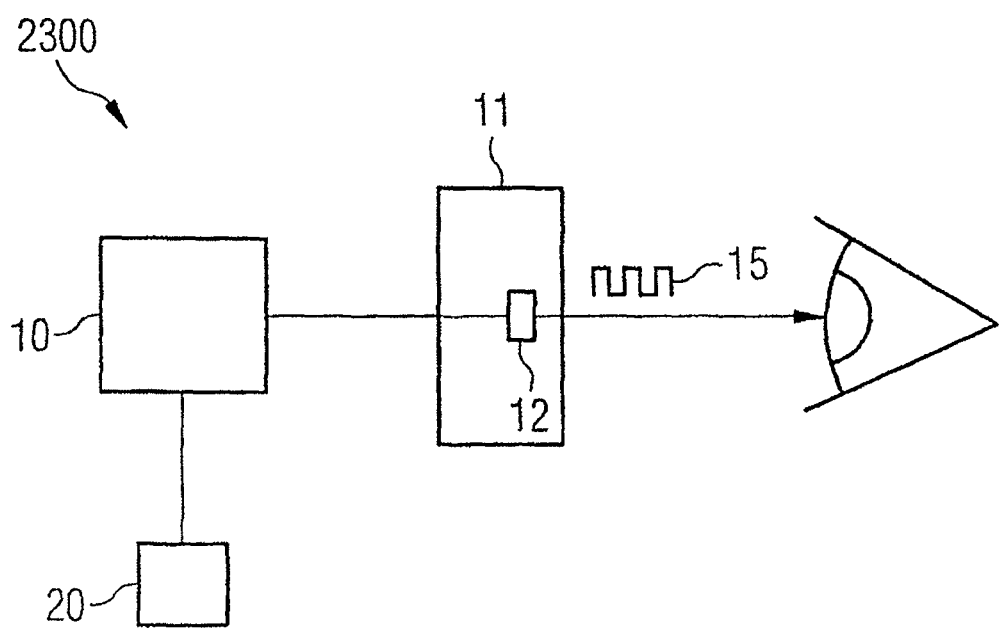
FIG. 23 shows a schematic illustration of a device 2300 as per a further exemplary embodiment.

FIG. 23 schematically illustrates a device 2300, which in large parts corresponds to the device 300 disclosed in FIG. 3, and whose structurally identical, or at least structurally similar, components have therefore been denoted by the same reference signs. Like the device 300, the device 2300 contains a stimulation unit 11, but unlike in the device 300 this unit need not necessarily contain at least two stimulation elements. By way of example, the device 2300 can only have a single stimulation element 12 for generating visual stimulation signals 15, but any larger number of stimulation elements can however also be provided. Similar to device 300 discussed above, the device 2300 comprises a measurement unit 20, which provides measurement signals recorded on the patient and transmits said signals to a control unit 10. The control unit 10 uses the measurement signals in order to generate control signals therefrom, by means of which the stimulation element or elements 12 are actuated.

The measurement unit 20 can involve non-invasive sensors, such as electroencephalography (EEG) electrodes, magnetoencephalography (MEG) sensors, accelerometers, electromyography (EMG) electrodes and sensors for determining blood pressure, respiration or skin resistance. Furthermore, the measurement unit 20 in the form of one or more sensors can be implanted into the body of the patient. By way of example, epicortical, intracortical or subcutaneous electrodes can be used as invasive sensors. In particular, the measurement unit 20 can be used to measure the physiological activity in the stimulated target region or in a region connected therewith.

The device 2300 can be used for desynchronization of a neuron population with a pathologically synchronous and oscillatory neuronal activity. The device 2300 can have the same refinements as the device 300.

The measurement signals recorded by the measurement unit 20 can be converted directly or if need be after one or more processing steps into visual stimulation signals 15 and can be applied by the stimulation unit 11. By way of example, the measurement signals, amplified and if need be after mathematical combination (e.g. after mixing the measurement signals) with a time delay and linear and/or nonlinear combination steps, can be used as control signals for the stimulation unit 11. Herein, the combination mode can be selected such that the pathological neuronal activity is counteracted and the stimulation signal likewise disappears or is at least significantly reduced in strength as the pathological neuronal activity reduces.

Hereinbelow, linear and nonlinear processing steps are described, by means of which the measurement signals obtained with the aid of the measurement unit 20 can be processed before they are fed into the control input or inputs of the stimulation element or elements 12. Both the linear and the nonlinear processing steps can equally be used both in the device 300 and in the device 2300. In the case of a nonlinear processing of the measurement signals, it is not the phase of the neuronal activity that is reset in the respective stimulated subpopulations, but it is the synchronization in the pathologically active neuron population that is suppressed by influencing the saturation process of the synchronization.

In the case of linear processing of a measurement signal obtained by the measurement unit 20, the measurement signal can, for example, be filtered and/or amplified and/or acted upon with a time delay before the signal processed in this fashion is used to actuate the stimulation unit 11 or the stimulation elements 12 (and 13) arranged in the stimulation unit 11. In an exemplary embodiment, it is assumed that the measurement signal was recorded by means of an epicortical or intracortical electrode and reproduces the pathological activity in the target area. Accordingly, the measurement signal is a sinusoidal oscillation with a frequency in the range between 1 and 30 Hz. It is furthermore assumed in an exemplary fashion that the measurement signal has a frequency of 5 Hz. The measurement signal can be filtered by means of a band-pass filter with a transmission region in the vicinity of 5 Hz and can be amplified by means of an amplifier such that it has suitable levels for actuating the stimulation unit 11. The amplified sinusoidal oscillation obtained thereby is subsequently used for actuating the stimulation unit 11. Transferred to the stimulation method shown in FIG. 11, this means that the rectangular stimulation signals 45 are replaced in this case by a sinusoidal oscillation at a frequency of 5 Hz.

Provided that a plurality of stimulation elements are used for the stimulation, the measurement signal can be acted upon by the delays τ shown in FIG. 11 before said signal is fed into the corresponding stimulation elements as a control signal.

The following text explains with the aid of an example how a measurement signal obtained by the measurement unit 20 can be subjected to nonlinear processing before it is used as an actuation signal for the stimulation unit 11. Similar to linear processing, the measurement signal can in this case also be filtered and/or amplified and/or acted upon by a time delay.

The start point is an equation for the actuation signal S(t):

$$S(t) = K \cdot \overline{Z}^2(t) \cdot \overline{Z}^*(t-\tau) \tag{1}$$

In equation (1), K is an amplification factor that can be selected in a suitable fashion and $\overline{Z}(t)$ is an average state variable of the measurement signal. $\overline{Z}(t)$ is a complex variable and can be represented as follows:

$$\overline{Z}(t) = X(t) + iY(t), \tag{2}$$

wherein X(t) can correspond to e.g. the neurological measurement signal. Since the considered frequencies lie in the vicinity of 10 Hz=1/100 ms=1/$T_\alpha$, the imaginary part Y(t) can be approximated by X(t−$\tau_\alpha$), wherein for example $\tau_\alpha$=$T_\alpha$/4 holds true. This results in:

$$S(t) = K \cdot [X(t) + iX(t-\tau_\alpha)]^2 \cdot [X(t-\tau) - iX(t-\tau-\tau_\alpha)]. \tag{3}$$

Equation (3) can be rewritten as follows:

$$S(t) = K \cdot [X(t)^2 \cdot X(t-\tau) + i2X(t) \cdot X(t-\tau_\alpha) \cdot X(t-\tau) - \\ X(t-\tau_\alpha) \cdot X(t-\tau) - iX(t-\tau-\tau_\alpha) \cdot X(t)^2 + \\ 2X(t) \cdot X(t-\tau_\alpha) \cdot X(t-\tau-\tau_\alpha) + iX(t-\tau-\tau_\alpha) \cdot X(t-\tau_\alpha)]. \tag{4}$$

The real part of equation (4) is used as the actuation signal for the stimulation unit 11:

$$\text{real}[S(t)] = K \cdot [X(t)^2 \cdot X(t-\tau) - X(t-\tau_\alpha) \cdot X(t-\tau) + 2X(t) \cdot X(t-\tau_\alpha) \cdot X(t-\tau-\tau_\alpha)] \tag{5}$$

While the foregoing has been described in conjunction with an exemplary embodiment, it is understood that the term "exemplary" is merely meant as an example, rather than the best or optimal. Accordingly, the application is intended to cover alternatives, modifications and equivalents, which may be included within the spirit and scope of the disclosure herein.

Additionally, in the preceding detailed description, numerous specific details have been set forth in order to provide a thorough understanding of the present application. However, it should be apparent to one of ordinary skill in the art that the present device and method disclosed herein may be practiced without these specific details. In other instances, well-known methods, procedures, components, and circuits have not been described in detail so as not to unnecessarily obscure aspects of the present application.

The invention claimed is:

1. A device for stimulating subpopulations of a patient's neuron population, the device comprising:
   a stimulation unit including N stimulation elements, each configured to generate respective visual stimulation pulses at different spatial locations corresponding to respective prescribed locations in a visual field of the patient such that the visual stimulation pulses are transmitted to respective subpopulations of the neuron population via an optic nerve of the patient when the visual stimulation pulses are visually received by the patient; and
   a control unit configured to sequentially actuate each of the N stimulation elements of the stimulation unit to generate the visual stimulation pulses at a repeating periodic frequency $f_{stim}$ that is between 1 and 30 Hz, where N is an integer and where $T_{stim}$ is equal to $1/f_{stim}$,
   wherein the control until actuates each of the N stimulation elements to generate the visual stimulation pulses for a time period between $T_{stim}/2-T_{stim}/10$ and $T_{stim}/2+T_{stim}/10$, and
   wherein the N stimulation elements are sequentially actuated to generate the visual stimulation pulses with a time offset that is approximately $1/(f_{stim} \times N)$ seconds between respective visual stimulation pulses in the sequence of the visual stimulation pulses generated by the N stimulation elements.

2. The device as claimed in claim 1, wherein the stimulation unit is a pair of transmission glasses having a pair of lenses.

3. The device as claimed in claim 2, wherein the lenses include a plurality of segments and the control unit is further configured to control the transmission properties of the segments.

4. The device as claimed in claim 1, wherein the stimulation unit is a pair of glasses including a plurality of light sources.

5. The device as claimed in claim 4, wherein the glasses have a transparent region.

6. The device as claimed in claim 4, wherein the glasses are opaque.

7. The device as claimed in claim 1, further comprising a measurement unit with at least one sensor configured to record measurement signals relating to physiological activity of the patient.

8. The device as claimed in claim 7, wherein the control unit is further configured to actuate the stimulation elements based on the measurement signals such that the stimulation elements convert the measurement signals into visual stimulation pulses.

9. The device as claimed in claim 7, wherein the control unit is further configured to process the measurement signals linearly or nonlinearly and to the processed measurement signals into control inputs of the stimulation elements.

10. The device as claimed in claim 7, wherein the control unit is further configured to determine, depending on the measurement signals, whether the stimulation elements generate the respective visual stimulation pulses.

11. The device as claimed in one of claim 7, wherein the at least one sensor is at least one of an EEG electrode, an MEG sensor, an accelerometer, an EMG electrode, a sensor configured to determine blood pressure, a sensor configured to determine respiration, a sensor configured to determine skin resistance, epicortical electrode, an intracortical electrode; and a subcutaneous electrode.

12. The device as claimed in claim 1, wherein N is equal to or greater than 2.

13. The device as claimed in claim 1, wherein the repeating periodic frequency $f_{stim}$ is a mean frequency of pathologically rhythmic activity of the subpopulations of the patient's neuron population.

14. A method for stimulating subpopulations of a patient's neuron population, the method comprising:
    generating, by N stimulation elements, respective visual stimulation pulses at different spatial locations corresponding to respective prescribed locations in a visual field of the patient such that the visual stimulation pulses are transmitted to respective subpopulations of the neuron population when the visual stimulation pulses are visually received by the patient; and
    controlling the sequence of the respective visual stimulation pulses generated by each of the N stimulation elements to generate the visual stimulation pulses at a repeating periodic frequency $f_{stim}$ that is between 1 and 30 Hz, where N is an integer and where $T_{stim}$ is equal to $1/f_{stim}$,
    wherein the visual stimulation pulses are generated for a time period between $T_{stim}/2-T_{stim}/10$ and $T_{stim}/2+T_{stim}/10$, and
    wherein the N stimulation elements are sequentially actuated to generate the visual stimulation pulses with a time offset that is approximately $1/(f_{stim} \times N)$ seconds between respective visual stimulation pulses in the sequence of the visual stimulation pulses generated by the N stimulation elements.

15. The method as claimed in claim 14, wherein N is equal to or greater than 2.

16. The method as claimed in claim 14, further comprising setting the repeating periodic frequency $f_{stim}$ to a mean frequency of pathologically rhythmic activity of the subpopulations of the patient's neuron population.

* * * * *